United States Patent [19]
Lesage-Meessen et al.

[11] Patent Number: 6,162,637
[45] Date of Patent: Dec. 19, 2000

[54] ASPERGILLUS NIGER WHICH PRODUCES VANILLIC ACID FROM FERULIC ACID

[75] Inventors: Laurence Lesage-Meessen; Michel Delattre; Mireille Haon, all of Marseille; Marcel Asther, La Ciotat, all of France

[73] Assignee: Institut National de la Recherche Agronomique - I.N.R.A., Paris, France

[21] Appl. No.: 09/216,031

[22] Filed: Dec. 18, 1998

Related U.S. Application Data

[62] Division of application No. 08/793,899, filed as application No. PCT/FR95/01173, Sep. 13, 1995, Pat. No. 5,866,380.

[30] Foreign Application Priority Data

Sep. 13, 1994 [FR] France ..................... 94/10889

[51] Int. Cl.⁷ ................. C12N 1/14; C12P 7/42
[52] U.S. Cl. ............ 435/254.3; 435/146; 435/917
[58] Field of Search ................ 435/254.3, 917, 435/146

[56] References Cited

U.S. PATENT DOCUMENTS 5,128,253  7/1992  Labuda et al. .
5,262,315  11/1993  Gross et al. .
5,279,950  1/1994  Labuda et al. .

FOREIGN PATENT DOCUMENTS 453368  10/1991  European Pat. Off. .

OTHER PUBLICATIONS

Middelhoven, Wouter J., "Catabolism of benzene compounds by ascomycetous and basidiomycetous yeasts and yeastlike fungi: a literature review and an experimental approach", *Chemical Abstracts*, vol. 120, No. 19, May 9, 1994, Abstract No. 239831, pp. 498–499.

Falconnier, B. et al., "Vanillin as a product of ferulic acid biotransformation by the white–rot fungus Pycnoporus cinnbarinus I–937: Identification of metabolic pathways", *Chemical Abstracts*, vol. 121, No. 23, Dec. 5, 1994, Abstract No. 276417, p. 590.

*Primary Examiner*—Sandra E. Saucier
*Attorney, Agent, or Firm*—Alston & Bird LLP

[57] ABSTRACT

Method for the production of vanillic acid and vanillin by bioconversion from ferulic acid in a medium containing phospholipids cultured with at least one microorganism from the classes Ascomycetes, Basidiomycetes or Actinomycetes. Vanillin is also produced by bioconversion of vanillic acid by at least one microorganism of the class Basidiomycetes in a medium containing cellobiose.

1 Claim, No Drawings

ASPERGILLUS NIGER WHICH PRODUCES VANILLIC ACID FROM FERULIC ACID

CROSS-REFERENCE TO RELATED APPLICATIONS

This application is a divisional of application Ser. No. 08/793,899 filed Jun. 12, 1997 now U.S. Pat. No. 5,866,380, which application is a 371 of PCT/FR95/01173 filed Sep. 13, 1995.

BACKGROUND OF THE INVENTION

The present invention relates to the obtaining of vanillic acid and vanillin by bioconversion.

At the present time, vanillin is the flavouring most widely used in the agri-foodstuffs industries. However, the production of natural vanillin from vanilla pods covers only 20% of the market requirements, and its production cost is of the order of 25,000 FF/kg.

Vanillin may also be obtained by chemical synthesis; however, this method of obtaining the product, while suitable for the manufacture of perfumes and cosmetics, may give rise to legislative problems in the agri-foodstuffs industries. In addition, synthetic flavourings tend, moreover, to be less well liked by consumers than flavourings of natural origin.

Accordingly, an effort is being made to obtain aromatic compounds produced by means of biological processes, which employ microorganisms (bacteria, yeasts, fungi), animal or plant cells or their enzyme systems.

Vanillin is produced by certain plants and microorganisms, especially fungi, where it constitutes one of the degradation products of precursors containing an aromatic ring (ferulic acid and vanillic acid).

European Patent Application 453 368 in the name of the company PERNOD-RICARD describes the production of natural vanillin by bioconversion of ferulic acid or vanillic acid in the presence of a filamentous fungus of the Basidiomycetes group, *Pycnoporus cinnabarinus*.

In this fungus, four metabolic pathways of conversion of ferulic acid have been identified:

Pathway 1: ferulic acid is reduced to coniferyl aldehyde and then to coniferyl alcohol; thereafter different dimers are formed from this compound. This is a minor pathway.

Pathway 2: cleavage of the propenoic chain of ferulic acid takes place, with the loss of two carbons and formation of vanillic acid.

Pathway 3: the vanillic acid resulting from pathway 2 is reduced to vanillin by the reductase I. The vanillin produced may then be reduced by the reductase II to vanillyl alcohol.

Pathway 4: the vanillic acid resulting from pathway 2 is hydroxylated and decarboxylated to methoxyhydroquinone by the action of an intracellular vanillate hydroxylase.

Under the conditions described in Application EP 453 368, the production of vanillin by *P. cinnabarinus* MIC11 from 300 mg/l of ferulic acid is at most of the order of 45 mg/l (molar conversion yield of 20.5%), and from 300 mg/l of vanillic acid this production is at most of the order of 81.4 mg/l (molar conversion yield of 31%).

SUMMARY OF THE INVENTION

The object of the present invention is to improve the yield of the production of natural vanillin by bioconversion from precursors containing an aromatic ring (ferulic acid and vanillic acid). To this end, the inventors have sought to improve the yield of conversion of ferulic acid to vanillic acid, and the yield of conversion of vanillic acid to vanillin.

The subject of the present invention is a process for obtaining vanillic acid by bioconversion from ferulic acid, which process is characterized in that the said bioconversion is performed using a culture comprising at least one strain of a filamentous fungus chosen from the group consisting of Ascomycetes and Basidiomycetes, or at least one actinomycete strain.

The subject of the present invention is also a process for obtaining vanillin by bioconversion from ferulic acid, which process is characterized in that it comprises:

a step of conversion of ferulic acid to vanillic acid by the process defined above;

a step of conversion of vanillic acid to vanillin by at least one filamentous fungus of the class Basidiomycetes.

According to a first variant of the process for obtaining vanillin according to the invention, the two steps are performed sequentially. In this case, the process according to the invention comprises:

a step during which ferulic acid is added to a culture comprising at least one strain of a filamentous fungus chosen from the group consisting of Ascomycetes and Basidiomycetes, or at least one actinomycete strain, and the vanillic acid produced is collected;

a step during which the vanillic acid produced during the first step is added to a culture comprising at least one strain of a filamentous fungus of the class Basidiomycetes, and the vanillin produced is collected.

To carry out this variant, the fungi used in each of the steps are cultured separately until a biomass is obtained possessing the capacities needed for the bioconversion (that is to say a biomass of at least 0.5 g of dry matter per litre of culture), and the cultures obtained are then used successively.

According to a second variant of the process according to the invention, the two steps are performed simultaneously. In this case, ferulic acid is added to a culture comprising, for the conversion of ferulic acid to vanillic acid, at least one strain of a filamentous fungus chosen from the group consisting of Ascomycetes and Basidiomycetes, or at least one actinomycete strain, and, for the conversion of vanillic acid to vanillin, at least one Basidiomycetes strain which can be identical to or different from the one used to convert ferulic acid to vanillic acid, and the vanillin produced is collected.

To carry out this second variant, the fungi used for the conversion of ferulic acid to vanillic acid and those used for the conversion of vanillic acid to vanillin are cultured separately until a biomass is obtained possessing the capacities needed for the bioconversion, and the cultures obtained are then pooled to obtain a coculture enabling the bioconversion to be carried out in a single step.

For the bioconversion of ferulic acid to vanillic acid, preferred ascomycetes belong to the genera Eurotium, Penicillium and Aspergillus; preferred basidiomycetes belong to the genera Bjerkandera, Nidula, Nidularia, Phanerochaete, Pycnoporus, Trametes, Lentinus and Ischnoderma; preferred actinomycetes belong to Streptomyces.

For the bioconversion of vanillic acid to vanillin, preferred basidiomycetes belong to the genera Bjerkandera, Nidula, Nidularia, Phanerochaete, Pycnoporus, Trametes, Lentinum and Ischnoderma.

DETAILED DESCRIPTION

Table I below lists, without implied limitation, a few species suitable for carrying out the process according to the invention, and a few strains tested by the inventors, and which have proved especially efficacious in this context.

TABLE I

| Species | Example of strains used |
|---|---|
| Actinomycetes: | |
| Streptomycetes setonii | ATCC 25497 |
| Ascomycetes: | |
| Eurotium chevalieri | |
| Penicillium verrucosum cyclopium | |
| Aspergillus oryzae | |
| Aspergillus versicolor | |
| Aspergillus niger | LMTC No. 2.7 (CNCM I-1472) |
| Basidiomycetes | |
| Ischnoderma benzoimum | CBS 250.30 |
| Bjerkandera adusta | CBS 595.79 |
| Nidula niveo-tomentosa | ATCC 38357 |
| Phanerochaete sordida | IHEM 3730 |
| Phanerochaete chrysosporium | MIC 247 (CNCM I-1471) |
| Pycnoporus cinnabarinus | MUCL 38467 |
| Trsmetes pini | CBS 210.36 |
| Lentinus edodes | CBS 454.59 |

It is possible, depending on the case, to obtain the different strains mentioned from the MUCL collection, 3 place Croix du Sud, 1348, Louvain La Neuve, Belgium, from the IHEM collection, 14 rue J. Wytsman, 1050, Brussels, Belgium, from the CBS collection, Oosterstraat 1, Postbus 273, NL-3740 AG Baarn and from the ATCC collection, 12301 Parklawn Drive, Rockville, Md. 20852 U.S.A.

Moreover, the *Aspergillus niger* strain LMTC 2.7 and the *Phanerochaete chrysosporium* strain MIC 247 were deposited on Aug. 31, 1994 with the CNCM (Collection Nationale de Cultures de Microorganisms [National Collection of Microorganism Cultures]) held by the Pasteur Institute, 26 rue du Docteur Roux, Paris, under the respective numbers I-1472 and I-1471.

The organisms may be cultured in the form of free cells, or in the form of cells immobilized on a hydrophilic or hydrophobic support which is preferably rough.

Culturing is performed, in a conventional manner, starting from an inoculum which can consist of spores, of fragments of mycelium or of a mycelium preculture. The culture medium contains a carbon source, at least one nitrogen source and inorganic salts, and yeast extract is added to it. The constituents of this medium can be the ones which are conventionally used for culturing the species of fungus in question.

However, the inventors found that, when the carbon source used comprises or consists of at least one phospholipid, an acceleration of the bioconversion is observed, especially as regards the bioconversion of ferulic acid to vanillic acid.

Advantageously, the culture medium comprises at least one phospholipid chosen from the group consisting of phosphatidylcholine, lysophosphatidylcholine, phosphatidylethanolamine, acylphosphatidylethanolamine, phosphatidylinositol and phosphatidic acid.

Preferably, this phospholipid or mixture of phospholipids is used at a concentration of between 0.1 and 20 g/l.

For example, it is possible to use a mixture of soya phospholipids comprising:

12% of phosphatidylcholine and lysophosphatidylcholine;

31% of phosphatidylethanolamine and acylphosphatidylethanolamine;

27% of phosphatidylinositol;

30% of phosphatidic acid.

To improve the yield of bioconversion of ferulic acid to vanillic acid, it is also possible to activate peroxysomal beta-oxidation.

The inventors observed, in addition, that the use of cellobiose as sole carbon source for the fungus, or as a supplement to another carbon source, for example to a sugar such as maltose, enables the production of methoxyhydroquinone to be limited very significantly, and hence the yield of bioconversion of vanillic acid to vanillin to be increased.

According to a preferred embodiment of the process according to the invention, the carbon source used comprises or consists of cellobiose.

According to a preferred arrangement of this embodiment, the culture medium comprises cellobiose.

The cellobiose may be added from the start of culturing, at a concentration of between 0.5 g/l and 10 g/l, and preferably 5 g/l, and/or shortly before or simultaneously with the addition of ferulic acid or vanillic acid, at a concentration in this case of between 0.5 g/l and 5 g/l, and preferably 2.5 g/l.

To initiate the bioconversion, the precursor is added to the culture, this being either ferulic acid, followed by vanillic acid, in the case of the first variant of the process, or ferulic acid in the case of the second variant of the process.

It is advantageous to add, at the same time as the precursor, an amount between 0.01 and 5 g/l of at least one product constituting a carbon source or a nitrogen source, or of inorganic salts or of lipids or of a mixture of these different products.

Among carbon sources which can be used for this purpose, there may be mentioned maltose, cellobiose, galacturonic acid, xylose, rhamnose, arabinose; among nitrogen sources, diammonium tartrate, yeast extract; among inorganic salts, calcium, potassium and magnesium salts; among lipids, emulsified fatty acids and phospholipids.

Ferulic acid is a readily available and inexpensive starting material. It is present, for example, in the cell wall fraction of agricultural by-products such as beet pulps (0.9% of the dry weight) or cereal brans (2.0% of the dry weight in maize brans). Vanillic acid can, in particular, be produced from ferulic acid during the first step of the process according to the invention.

The ferulic acid may be used in free form or alternatively in bound form; bound ferulic acid is understood to mean an ester of a sugar or of an oligosaccharide with ferulic acid.

The free ferulic acid or the vanillic acid may be added as they are, in the form of crystals, or in the form of a solution of their sodium, potassium or ammonium salts.

According to a preferred embodiment of the process according to the invention, ferulic acid or vanillic acid is added in the proportion of 0.1 to 2 g/l of culture, and preferably 0.3 g/l. If bound ferulic acid is used, or alternatively a ferulic acid or vanillic acid salt, the concentration will be adjusted so as to correspond to the range of ferulic acid or vanillic acid concentrations indicated above.

According to another preferred embodiment of the process according to the invention, the addition of ferulic acid or of vanillic acid takes place after 12 to 96 h of culture. However, when addition in a single portion would lead to concentrations which are toxic to the fungus, then the concentrations above 2 g/l for ferulic acid and above 2 g/l for vanillic acid, sequential or continuous additions will be performed.

The inventors observed, in addition, that it was possible and especially advantageous to carry out the process according to the invention in the presence of a nonionic resin, preferably of the hydrophobic type. In effect, not only vanillic acid but also vanillin are toxic to the fungi at concentrations above 2 g/l. The use of resin enables these metabolites to be trapped and their concentrations to be maintained below the threshold of toxicity.

Moreover, the use of resin to trap the vanillin also enables the latter to be removed from the reaction mixture before it is reduced to vanillyl alcohol.

The vanillic acid or vanillin bound to the resin may be recovered by elution with a suitable solvent such as, for example, ethanol.

Some nonionic resins which can be used are, by way of example without implied limitation, the following:

Amberlite resins: XAD2; XAD4; XAD7;

Duolite resin: XAD761;

Dowex resin: S112.

The resins XAD761 and S112 are preferred for binding vanillic acid, and the resins XAD2, XAD4, XAD7 and S112 are preferred for binding vanillin.

As an example, the resin XAD2 enables 98% of the vanillin to be bound; the adsorption capacity of this resin is of the order of 20 mg of vanillin per gram of resin.

Preferably, the addition of resin is performed as soon as vanillin has appeared.

The addition of resin may take place, for example, either directly into the culture vessel, or by circulating the culture medium through an external loop containing the resin.

To remove the vanillic acid and the vanillin from the culture medium and recover them as they are being produced, it is also possible to make use of other techniques such as ultrafiltration, reverse osmosis or uptake on active charcoal.

To improve significantly the yield of bioconversion of vanillic acid to vanillin, it is also possible to choose a Basidiomycetes strain which forms only a very small amount of vanillyl alcohol and accumulates the vanillin produced.

Such a strain is to be found, for example, in basidiomycetes of the order Nidulariales.

Since the vanillin produced very quickly becomes toxic for the metabolism of the fungus, it is advantageous in this case to trap it using a resin, as mentioned above.

A better understanding of the present invention will be gained from the additional description which follows, which refers to examples of implementation of the process according to the invention.

It should, however, be clearly understood that these examples are given only by way of illustration of the subject of the invention, of which they in no way constitute a limitation.

EXAMPLE 1

Production of Cultures

A) Fungi:

The composition of the base medium is given below:
Composition of the medium:

| | |
|---|---|
| Maltose | 20 g/l |
| Diammonium tartrate | 1.842 g/l |
| KH$_2$PO$_4$ | 0.2 g/l |
| CaCl$_2$.2H$_2$O | 0.0132 g/l |
| MgSO$_4$.7H$_2$O | 0.5 g/l |
| Yeast extract | 0.5 g/l |

The medium is sterilized by autoclaving for 20 min at 120° C.

Inoculation is performed with mycelial fragments, spores (2×10$^5$ spores/ml) or a mycelium precultures as described in Application EP 453 368.

After inoculation, the cultures are incubated at 30° C. and subjected to stirring at 120 rpm.

After 12 to 96 h of culture, ferulic acid or vanillic acid (in the case of carrying out the process in two steps) is added. The acids are used in salt form in solution in water; the solution was sterilized beforehand by filtration (0.2 µm membrane). The solution is added in a sufficient amount to obtain a final concentration corresponding to 0.3 g of ferulic acid or a vanillic acid per litre of culture.

B) Actinomycetes:

The composition of the base medium is as follows:

| | |
|---|---|
| Glycerol | 5 g/l |
| Yeast extract | 2 g/l |

The medium is sterilized by autoclaving for 20 min at 120° C.

Inoculation is performed with fragments of aerial mycelium taken from a malt/agar solid medium.

After inoculation, the cultures are incubated at 30° C. and subjected to stirring at 120 rpm.

Ferulic acid in salt form is added at the very beginning of culturing, at a concentration of 1 g/l.

C) Monitoring of the bioconversion:

The bioconversion taking place when the process according to the invention is carried out is monitored by assaying the metabolites produced. To carry out this assay, an aliquot of the culture medium is withdrawn under sterile conditions at regular time intervals. This aliquot is then filtered (0.2 µm membrane), and an HPLC analysis of the filtrate is carried out in order to detect and assay the metabolites produced.
Conditions of HPLC analysis
  reversed phase=Bondapak C18 column
  solvent: 0.01% CH$_3$COOH in H$_2$O/methanol
  UV detection at 280 nm

EXAMPLE 2

Bioconversion of Ferulic Acid to Vanillic Acid

A) By a fungus

The *Aspergillus niger* strain MIC 373, deposited on Aug. 31, 1994 with the Collection Nationale de Culture de Microorganismes [National Collection of Microorganism Cultures] under the number I-1472, was cultured as described in Example 1 above.

Ferulic acid was added in continuous fashion in the proportion of 430 mg/l per 24 hours.

Ferulic acid and its metabolites are assayed as described in Example 1 above.

The results obtained after 15 days of growth of the culture are shown in Table II below.

Legend to Table II:
Column 1: Ferulic acid consumed (mg/l);
Column 2: Vanillic acid produced (mg/l);
Column 3: Methoxyhydroquinone produced (mg/l);
Column 4: Molar yield (%); the molar yield is defined as the number of moles of vanillic acid produced for 100 mol of ferulic acid consumed.

TABLE II

| 1 | 2 | 3 | 4 |
|---|---|---|---|
| 5055 | 3600 | 109 | 82 |

A total consumption of the ferulic acid added is observed. A large majority (82%) of the latter is converted to vanillic acid, a small amount (2%) of which is metabolized to methoxyhydroquinone, and none at all to vanillin and vanillyl alcohol.

B) By an actinomycete:

The *Streptomyces setonii* strain ATCC 25497 was cultured as described in Example 1 above.

Ferulic acid in salt form is added at the very beginning of culturing, at a concentration of 1 g/l.

Ferulic acid and its metabolites are assayed as described in Example 1 above.

The results obtained after 100 hours of growth of the culture are shown in Table III below.

Legend to Table III:
Column 1: Ferulic acid consumed (mg/l);
Column 2: Vanillic acid produced (mg/l);
Column 3: Molar yield (%).

TABLE III

| 1 | 2 | 3 |
|---|---|---|
| 880 | 332 | 43 |

EXAMPLE 3

Activation of the Bioconversion of Ferulic Acid to Vanillic Acid by Adding Soya Phospholipids The source of phospholipids used is NAT 89 supplied by the company Natterman Phospholipid GmbH (Cologne, Germany). The composition of NAT 89 is as follows:

12% of phosphatidylcholine and lysophosphatidylcholine
31% of phosphatidylethanolamine and acylphosphatidylethanolamine
27% of phosphatidylinositol
30% of phosphatidic acid NAT89 (20 g/l) was used as carbon source in place of maltose in *Aspergillus niger* cultures. The results obtained show a faster bioconversion of ferulic acid to vanillic acid.

EXAMPLE 4

Activation of the Bioconversion of Vanillic Acid to Vanillin by the use of Resin To illustrate this example, a representative strain of a Basidiomycetes species mainly producing vanillyl alcohol was chosen.

The strain used is the *Phanerochaete chrysosporium* strain MIC 247, deposited on Aug. 31, 1994 with the Collection Nationale de Culture de Microorganisms under the number I-1471. This strain was cultured as described in Example 1 above.

Vanillic acid was added sequentially, namely: 0.3 g/l at the end of 3 days of culture, then 0.3 g/l every day.

For experiment 2, sterile resin XAD2 (Amberlite) is added in the proportion of 10% (weight/volume) after 3 days+6 h of culture of the fungus, that is to say 6 h after adding vanillic acid (at a concentration of 300 mg/l).

Vanillic acid and its metabolites are assayed as described in Example 1 above.

The results shown in Table IV below are given after 4 days and 7 days (experiment 1) or after 6 days (experiment 2) of growth of the culture.

Legend to Table IV
Column 1: Experiment number and age of the culture;
Column 2: Vanillic acid consumed (mg/l);
Column 3: Vanillin produced (mg/l);
Column 4: Vanillyl alcohol produced (mg/l);
Column 5: Methoxyhydroquinone produced (mg/l);
Column 6: Molar yield (%); the molar yield is defined here as the number of moles of vanillin produced per 100 mol of vanillic acid consumed.

TABLE V

| 1 | 2 | 3 | 4 | 5 | 6 |
|---|---|---|---|---|---|
| No. 1 4 d | 277 | 125 | 89 | 17 | 50 |
| 7 d | 1545 | 3 | 762 | 175 | 0.2 |
| No. 2 6 d | 838 | 628 | 51 | 86 | 82 |

In experiment 1, a high production of vanillyl alcohol combined with the production of vanillin is observed from day four. On day seven, all the vanillin produced has been metabolized to vanillyl alcohol.

In experiment 2, the vanillin has been bound by the resin as it has been produced (94% of the vanillin produced has been bound to the resin used), before it could be converted to vanillyl alcohol.

EXAMPLE 5

Activation of the Bioconversion of Vanillic Acid to Vanillin by the use of Cellobiose To illustrate this example, a representative strain of a Basidiomycetes species mainly producing methoxyhydroquinone was chosen.

The strain used is the *Pycnoporus cinnabarinus* strain MUCL 38467. This strain was cultured as described in Example 1 above.

Vanillic acid was added sequentially, namely: 0.3 g/l at the end of 3 days of culture, then 0.3 g/l every day.

For experiment 1, the carbon source 1 used is maltose, at a concentration of 20 g/l.

For experiment 2, the carbon source used is cellobiose, in the proportion of 5 g/l.

Vanillic acid and its metabolites are assayed as described in Example 1 above.

The results after 7 days of growth of the culture are shown in Table V below.

Legend to Table V:
 Column 1: Experiment number;
 Column 2: Vanillic acid consumed (mg/l);
 Column 3: Vanillin produced (mg/l);
 Column 4: Methoxyhydroquinone produced (mg/l);
 Column 5: Vanillyl alcohol produced (mg/l);
 Column 6: Molar yield (%); the molar yield is defined as the number of moles of vanillin produced per 100 mol of vanillic acid consumed.

TABLE V

| 1 | 2 | 3 | 4 | 5 | 6 |
|---|---|---|---|---|---|
| No. 1 | 1198 | 166 | 709 | 30 | 15 |
| No. 2 | 941 | 481 | 62 | 70 | 59 |

In experiment 1, high productions of vanillin, but also of methoxyhydroquinone, are observed after 7 days.

In experiment 2, the use of cellobiose as carbon source has enabled the production of methoxyhydroquinone to be limited very significantly, and that of vanillin to be increased.

In a second series of experiments described below, where maltose is used as the main carbon source, the addition of cellobiose before adding the precursor also enables the production of methoxyhydroquinone to be limited very significantly, and that of vanillin to be increased.

The following media and culture conditions were used:

Maltose 1: Sole carbon source: maltose at a concentration of 20 g/l.

Maltose 2: Carbon source: maltose at a concentration of 20 g/l+addition of 0.25% (w/v) of cellobiose after 3 days of incubation, 2 h before the addition of vanillic acid.

Maltose 3: Carbon source: maltose at a concentration of 20 g/l+addition of 0.35% (w/v) of cellobiose after 3 days of incubation, 2 h before the addition of vanillic acid.

Maltose 4: Carbon source: maltose at a concentration of 20 g/l+addition of 0.5% (w/v) of cellobiose after 3 days of incubation, 2 h before the addition of vanillic acid.

Maltose 2C: Carbon source: maltose at a concentration of 20 g/l+addition of 0.25% (w/v) of cellobiose after 3 days, 4 days, 5 days and 6 days of incubation, each addition preceding by 2 hours the addition of vanillic acid.

Maltose 3C: Carbon source: maltose at a concentration of 20 g/l+addition of 0.35% (w/v) of cellobiose after 3 days, 4 days, 5 days and 6 days of incubation, each addition preceding by 2 hours the addition of vanillic acid.

Maltose 4C: Carbon source: maltose at a concentration of 20 g/l+addition of 0.5% (w/v) of cellobiose after 3 days, 4 days, 5 days and 6 days of incubation, each addition preceding by 2 hours the addition of vanillic acid.

The results are shown in Table VI below.
Legend to Table VI:
 Column 1: Experiment number;
 Column 2: Vanillic acid consumed (mg/l);
 Column 3: Vanillin produced (mg/l);
 Column 4: Methoxyhydroquinone produced (mg/l);
 Column 5: Vanillyl alcohol produced (mg/l);
 Column 6: Molar yield (%); the molar yield is defined here as the number of moles of vanillin produced per 100 mol of vanillic acid consumed.

TABLE VI

| 1 | 2 | 3 | 4 | 5 | 6 |
|---|---|---|---|---|---|
| Maltose 1 | 1198 | 166 | 709 | 30 | 14 |
| Maltose 2 | 1199 | 342 | 466 | 26 | 28 |
| Maltose 3 | 1192 | 447 | 350 | 27 | 37 |
| Maltose 4 | 1195 | 388 | 393 | 25 | 32 |
| Maltose 2C | 1198 | 583 | 541 | 76 | 49 |
| Maltose 3C | 1198 | 457 | 526 | 72 | 51 |
| Maltose 4C | 1197 | 642 | 476 | 62 | 54 |

EXAMPLE 6

Use of a Strain Producing Mainly Vanillin

To illustrate this example, a representative strain of a Basidiomycetes species accumulating vanillin was chosen.

The strain used is a *Nidula niveo-tomentosa* strain which is available from the ATCC under the number 38357. This strain was cultured as described in Example 1 above.

Vanillic acid was added sequentially, namely: 0.3 g/l at the end of 3 days of culture, then 0.3 g/l every day.

Vanillic acid and its metabolites are assayed as described in Example 1 above.

The results on day 8 of growth of the culture are shown in Table VII below.
Legend to Table VII:
 Column 1: Vanillic acid consumed (mg/l);
 Column 2: Vanillin produced (mg/l);
 Column 3: Vanillyl alcohol produced (mg/l);
 Column 4: Methoxyhydroquinone produced (mg/l);
 Column 5: Molar yield (%)

TABLE VII

| 1 | 2 | 3 | 4 | 5 |
|---|---|---|---|---|
| 1252 | 444 | 20 | 334 | 39 |

Since this strain accumulates the vanillin being produced, very little vanillyl alcohol is obtained.

To optimize the use of this strain, it is possible, on the one hand to trap the vanillin as it is being produced, for example using resins as described in Example 4 above, and on the other hand to add cellobiose in order to limit the amount of methoxyhydroquinone produced, as described in Example 5 above.

What is claimed is:

1. A biologically pure strain of *Aspergillus niger* strain deposited on Aug. 31, 1994 with the CNCM under the number I-1472.

* * * * *

UNITED STATES PATENT AND TRADEMARK OFFICE
CERTIFICATE OF CORRECTION

PATENT NO.    : 6,162,637
DATED         : December 19, 2000
INVENTOR(S)   : Lesage-Meessen et al.

It is certified that error appears in the above-identified patent and that said Letters Patent is hereby corrected as shown below:

Title page, [56] References Cited, OTHER PUBLICATIONS, lines 7-8, "cinnbarinus" should read --cinnabarinus--.

Column 8, line 29, "TABLE V" should read --TABLE IV--.

Signed and Sealed this

Eighth Day of May, 2001

Attest:

NICHOLAS P. GODICI

*Attesting Officer*    Acting Director of the United States Patent and Trademark Office